(12) United States Patent
Suzuki

(10) Patent No.: US 7,820,984 B2
(45) Date of Patent: Oct. 26, 2010

(54) MEASURING DEVICE AND MEASURING METHOD

(75) Inventor: Yoshimasa Suzuki, Kawasaki (JP)

(73) Assignee: Olympus Corporation, Tokyo (JP)

( * ) Notice: Subject to any disclaimer, the term of this patent is extended or adjusted under 35 U.S.C. 154(b) by 158 days.

(21) Appl. No.: 12/340,886

(22) Filed: Dec. 22, 2008

(65) Prior Publication Data

US 2009/0189087 A1    Jul. 30, 2009

(30) Foreign Application Priority Data

Dec. 26, 2007 (JP) .............................. 2007-333584

(51) Int. Cl.
*G01N 21/64* (2006.01)
(52) U.S. Cl. ................................................. 250/458.1
(58) Field of Classification Search ............. 250/458.1, 250/459.1, 337, 361 R; 356/432
See application file for complete search history.

(56) References Cited

U.S. PATENT DOCUMENTS

| | | | | |
|---|---|---|---|---|
| 2,813,203 A | * | 11/1957 | Machler | ..................... 374/130 |
| 3,704,951 A | * | 12/1972 | Chupp | ........................ 356/301 |
| 4,956,759 A | * | 9/1990 | Goldenberg et al. | ........ 362/297 |
| 2002/0024015 A1 | * | 2/2002 | Hoffmann et al. | ........... 250/311 |
| 2002/0070355 A1 | * | 6/2002 | Ota | ......................... 250/492.2 |
| 2005/0110996 A1 | * | 5/2005 | Sharpe et al. | ............... 356/338 |

FOREIGN PATENT DOCUMENTS

| | | |
|---|---|---|
| JP | 11-142335 | 5/1999 |
| JP | 2007-078574 | 3/2007 |

* cited by examiner

*Primary Examiner*—David P Porta
*Assistant Examiner*—Marcus H Taningco
(74) *Attorney, Agent, or Firm*—Pillsbury Winthrop Shaw Pittman, LLP

(57) ABSTRACT

A measuring device includes a light source, a holding member for holding a sample, a first concave mirror and a second concave mirror, the second concave mirror being arranged on the light path from the light source to the holding member, the first concave mirror being arranged vis-a-vis the second concave mirror with the holding member interposed between them, the first concave mirror and the second concave mirror being arranged with their concave surfaces facing each other, the first concave mirror being larger than the second concave mirror in terms of their outer dimensions.

10 Claims, 6 Drawing Sheets

US 7,820,984 B2

MEASURING DEVICE AND MEASURING METHOD

CROSS REFERENCES TO RELATED APPLICATIONS

The present invention contains subject matter related to Japanese Patent Application JP 2007-333584 filed in the Japanese Patent Office on Dec. 26, 2007, the entire contents of which being incorporated herein by reference.

BACKGROUND OF THE INVENTION

1. Field of the Invention

The present invention relates to a fluorescence measuring device for micro samples. More particularly, it relates to a measuring device and a measuring method that can efficiently measure an extremely small fluorescent spot on a microchip or the like.

2. Description of the Related Art

Researches are being made on the technology of LOC (Lab on a chip) of downsizing measuring devices that have conventionally been utilized and causing them to react with an extremely small amount of a liquid agent. A chip that is smaller than 10 to several cm square is employed with the LOC technology. Such a chip is typically made of plastic, glass or silicon and grooves are formed on the surface thereof. An agent solution and a sample are flowed respectively into the grooves and isolated by a very small quantity before they are subjected to a reaction to analyze the micro sample. A very small quantity of a sample (object of examination) such as blood can be prepared with this technique. Thus, the LOC technology provides advantages including that the quantity of the sample, that of the agent necessary for detecting the sample and that of the solid and liquid waste of consumables used for the detection are reduced and that the time necessary for the detect is generally shortened.

JP 2007-78574-A discloses a measuring device to be used for the LOC technology. The disclosed measuring device can detect fluorescence from a micro sample by irradiating the micro sample with excitation light.

SUMMARY OF THE INVENTION

In an aspect of the present invention, there is provided a measuring device including: a light source; a holding member for holding a sample; a first concave mirror; and a second concave mirror; wherein the second concave mirror being arranged on the light path from the light source to the holding member, the first concave mirror being arranged vis-a-vis the second concave mirror with the holding member interposed between them, the first concave mirror and the second concave mirror being arranged with their concave surfaces facing each other, and the first concave mirror being larger than the second concave mirror in terms of their outer dimensions.

Preferably, in a measuring device according to the present invention, the first concave mirror and the second concave mirror are arranged in such a way that their focal positions agree with each other.

Preferably, a measuring device according to the present invention further includes an optical system arranged between the light source and the first concave mirror to collimate light emitted from the light source, the diameter of the flux of collimated light being greater than the diameter of the second concave mirror.

Preferably, in a measuring device according to the present invention, the first concave mirror and the second concave mirror are cylindrical mirrors and the curvatures of the two cylindrical mirrors are aimed at the same direction.

Preferably, in a measuring device according to the present invention, the first concave mirror and the second concave mirror are paraboloidal mirrors.

In another aspect of the present invention, there is provided a measuring method including: a first irradiation step of making a tubular flux of collimated light strike a sample from one of the opposite sides thereof; a second irradiation step of reflecting the flux of collimated light toward the sample after passing through the sample and focusing it in the sample; a third irradiation step of reflecting light emitted from the sample, while being scattered, collimating it and making it strike the sample from the other side; the second irradiation step and the third irradiation step being repeated before detecting light from the sample.

DETAILED DESCRIPTION OF THE PREFERRED EMBODIMENTS

Figure 1:
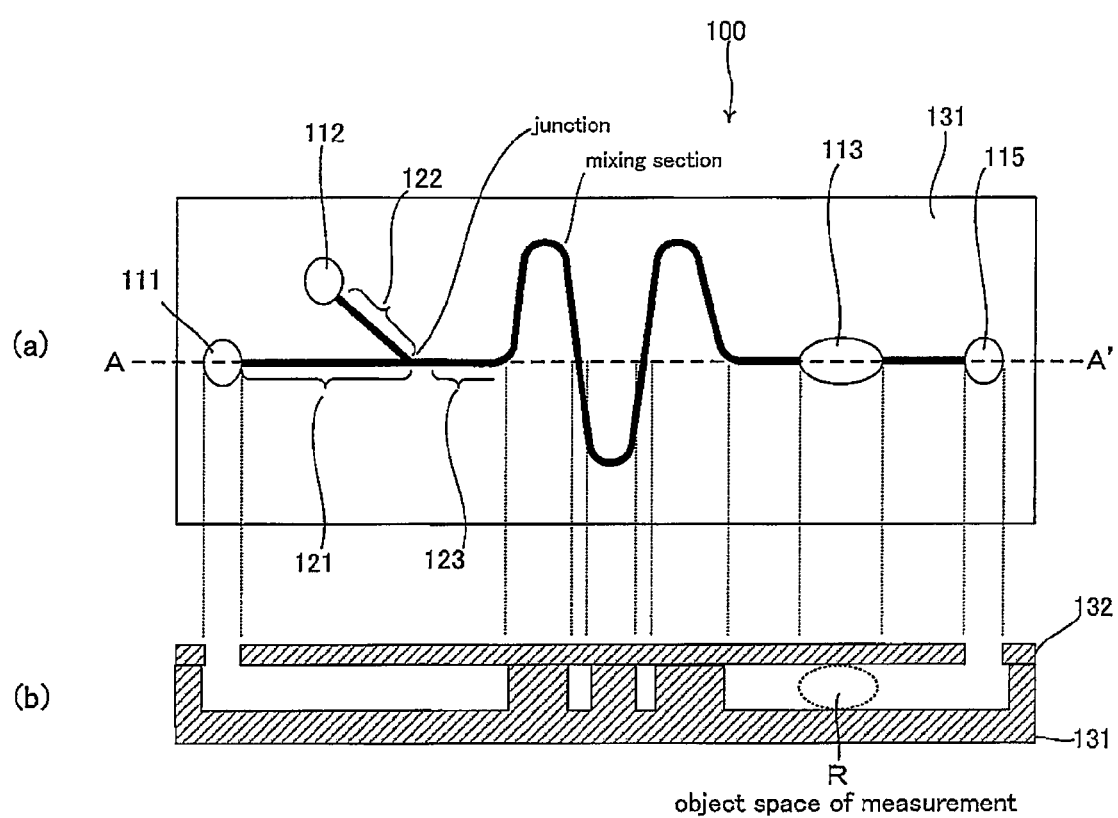
FIG. 1(a) and FIG. 1(b) are schematic illustrations of a microchip to be used in a measuring device according to a first embodiment of the present invention.

Now, preferred embodiments of the present invention will be described in greater detail by referring to the accompanying drawings. FIGS. 1(a) and 1(b) schematically illustrate a microchip. The microchip is adapted to be used in the measuring device according to the embodiment of the present invention. FIG. 1(a) is a schematic top view of the microchip, showing also flow channels. FIG. 1(b) is a schematic cross-sectional view of the microchip taken along line A-A' in FIG. 1(a). Referring to FIGS. 1(a),1(b) and FIG. 2, 100 generally denotes a microchip and 111, 112, 113 and 115 respectively denote a first liquid inlet port, a second liquid inlet port, a detecting section and a discharge port, while 121, 122 and 123 respectively denote a first flow channel, a second flow channel and a third flow channel and 131 and 132 respectively denote a first substrate and a second substrate.

The measuring device has an application, for instance, in measuring a tumor marker, any of various hormones or an antibody of a pathogenic bacterium. Measuring devices of this type are required to operate properly with a minimal quantity of sample (object of examination) for observation. A blood sample may be a typical example. The LOC (Lab on a chip) technology can introduce, agitate, measure and discharge a sample (object of examination) and an agent in the micro flow channels formed on a plastic-made substrate of a size of several cm. The microchip 100 shown in FIGS. 1(a) and 1(b) is an example that can be used with the LOC technology.

Micro flow channels are formed in the microchip 100 shown in FIGS. 1(a) and 1(b). The micro flow channels include a first flow channel 121, a second flow channel 122 and a third flow channel 123 that are linked to each other to form a letter of Y. The first flow channel is linked at an end thereof to a first liquid inlet port 111 for introducing first liquid and the second flow channel 122 is linked at an end thereof to a second liquid inlet port 112 for introducing second liquid. The third flow channel 123 has a mixing section in the inside for mixing the first liquid and the second liquid. The third flow channel 123 also has a detecting section 113 in the inside and a space R is formed in it (which space is to be referred to as object space of measurement hereinafter). The discharge port 115 can discharge a mixture of the first liquid and the second liquid.

A microchip 100 can be prepared by way of a process as described below. For example, a second substrate 132 where grooves that correspond to the above-described micro flow channels and a first substrate 131 where inlet ports (111, 112) and a discharge port 115 are formed are brought in. Then, the first substrate 131 and the second substrate 132 are bonded to each other. The substrates (131, 132) may typically be prepared by injection molding of injecting a resin material such as polystyrene (PS) or acryl resin (PMMA) from a metal mold. A semiconductor processing technique may be applied also to prepare a microchip 100. For instance, a microchip 100 may alternatively prepared by forming grooves that operate as micro flow channels on a silicon substrate by means of a micro processing technique such as anisotropic etching and subsequently bonding a closure member onto the substrate. Techniques for forming a microchip 100 by using a glass substrate are also known.

The dimensions of a microchip 100 that can be used for the purpose of the present invention may include outer dimensions of about 80 mm×60 mm×2.5 mm, while the micro flow channels has a width of about 0.5 mm and a depth of about 1 mm. For example, a sample (object of examination) may be introduced into the first liquid inlet port 111, while an agent is introduced into the second liquid inlet port 112. Then, the sample and the agent are merged at the junction of the two flow channels. The mixture liquid is then mixed well in the third flow channel 123 and a reproduced chemical reaction takes place there. The reaction is observed by a measuring device in the object space of measurement R.

An antigen/antibody reaction can be utilized when the measuring device is employed for an immunological test. More specifically, by adding a labeled antibody that emits light or fluorescence to the mixture solution, the intensity of fluorescence that is generated when excitation light is irradiated onto the mixture solution can be detected by means of a photodetector. For example, when a labeled antibody bonded to fluorescin is irradiated with excitation light of a wavelength of 495 nm, fluorescence of a wavelength of about 515 nm is generated and emitted.

Figure 2:
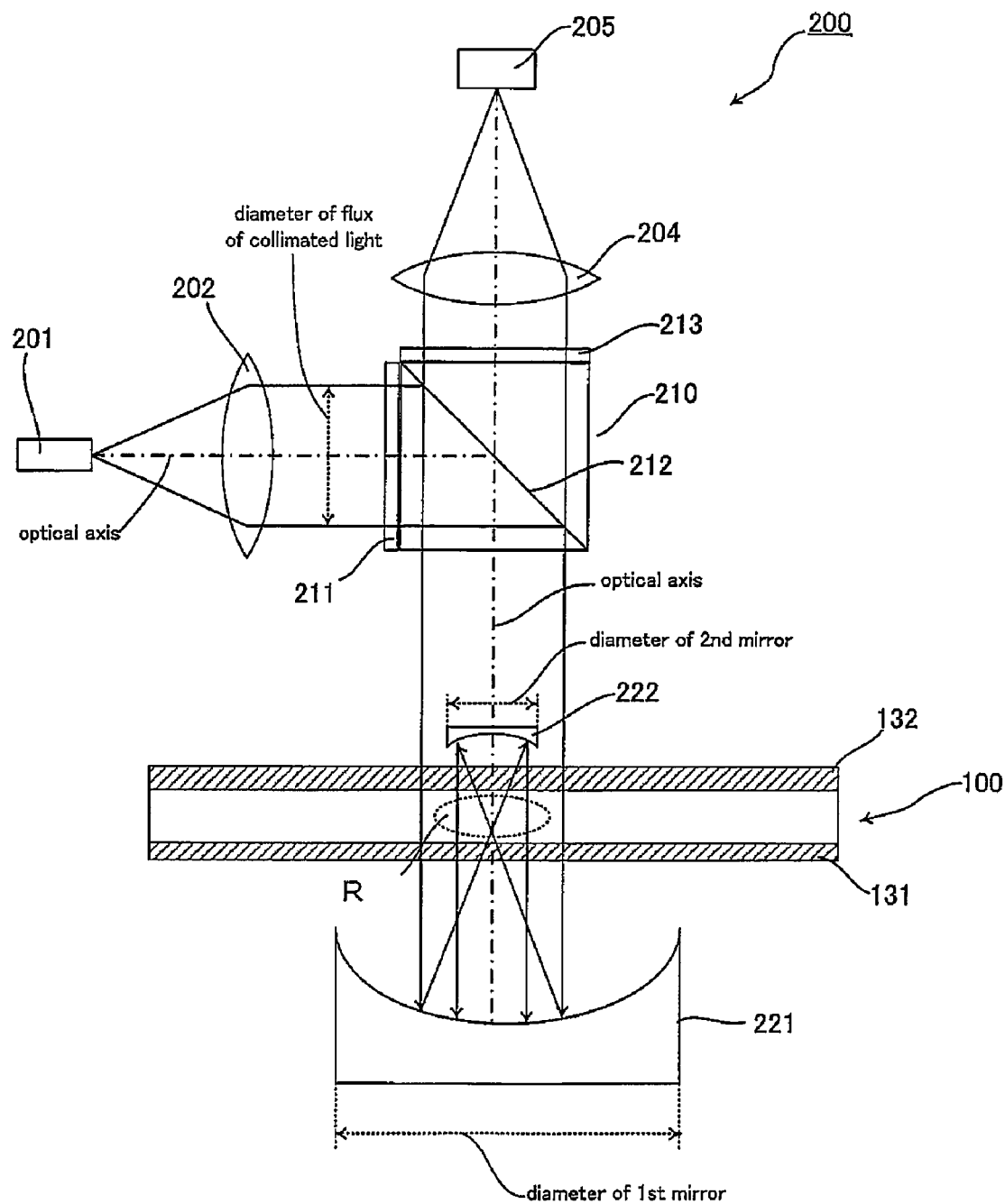
FIG. 2 is a schematic illustration of the measuring optical system of the measuring device according to the embodiment of FIG. 1, including a cross-sectional view of the detecting section of the measuring device.

Now, the measuring device of this embodiment will be described in terms of fluorescence measurement as an exemplar measurement. The measuring device of this embodiment measures the intensity of fluorescence that the fluorescent substance in the mixture liquid emits. FIG. 2 is a schematic illustration of the measuring optical system of the measuring device according to the present embodiment. FIG. 2 shows that a microchip 100 is set in position and the object space of measurement R is being observed.

In FIG. 2, 200 is the measuring device and 201 is a light source, while 202, 204, 205, 210, 211, 212, 213, 221 and 222 are respectively a collimator lens, a condenser lens, a photodetector, a fluorescence mirror unit, an excitation light selection filter, a dichroic mirror, a fluorescence selection filter, a first mirror and a second mirror.

The light source 201 emits light to be irradiated onto the microchip 100. The collimator lens 202 collimates light emitted from the light source 201. The collimator lens 202 is arranged on the optical path from the light source 201 to the microchip 100 and hence at the light emitting side of the light source 201. The fluorescence mirror unit 210 separates excitation light and fluorescence. The fluorescence mirror unit 210 is arranged on the light path from the collimator lens 202 to the microchip 100 and hence at the light emitting side of the collimator lens 202. The first mirror 221 and the second mirror 222 reflect and converge excitation light and also reflect fluorescence. The first mirror 221 and the second mirror 222 are arranged on the light path at the side of the microchip 100 relative to the fluorescence mirror unit 210. The microchip 100 is mounted on a stage (not shown), which stage is arranged on the light path from the first mirror 221 to the second mirror 222. The photodetector 205 receives fluorescence from the sample and detects the quantity of fluorescence. The photodetector 205 is arranged at the side opposite to the microchip 100 with the fluorescence mirror unit 210 interposed between them. The condenser lens 204 focuses fluorescence onto the photodetector 205. The condenser lens 204 is arranged between the photodetector 205 and the fluorescence mirror unit 210. The light source 201 emits light that includes excitation light. A halogen lamp may typically be employed for the light source 201. Other examples of light source 201 that can be used for the purpose of the present invention include a mercury lamp, a laser, a laser diode and an LED.

The collimator lens 202 collimates light emitted from the light source 201. The diameter of the flux of collimated light is greater than that of the second mirror 222. The expression of the diameter of the flux of collimated light as used herein refers to twice of the distance from the optical axis of the collimator lens 202 to the outermost boundary of the flux of light emitted from the collimator lens 202. The expression of the diameter of the second mirror 222 as used herein refers to twice of the distance from the outermost boundary of the reflection surface of the second mirror 222 to the optical axis of the second mirror 222. The collimator lens 202 can be omitted when a light source that can emit a flux of collimated light is employed. However, note that the diameter of the flux of collimated light is greater than the diameter of the second mirror 222 even when the collimator lens 202 is omitted. It is sufficient that the diameter of the flux of collimated light is greater than the diameter of the second mirror 222 at the position of the second mirror 222.

The fluorescence mirror unit 210 includes an excitation light selection filter 211, a dichroic mirror 212 and a fluorescence selection filter 213.

The excitation light selection filter 211 selectively transmits only light of a specific wavelength.

The dichroic mirror 212 has a characteristic property of reflecting excitation light transmitted through the excitation light selection filter 211 and another characteristic property of transmitting fluorescence. The dichroic mirror 212 is arranged at an angle of 45° relative to the light path at the side of the light source 201. Thus, excitation light that strikes the dichroic mirror 212 is deflected by 90° and directed to the microchip 100. When the predetermined space of the microchip 100 is the object space of measurement R, excitation light enters the object space of measurement R.

The fluorescence selection filter 213 may be selected from a band pass filter, an absorption filter or some other filter that has appropriate optical characteristics according to the wavelength band of the fluorescent substance to be detected.

Fluorescence emitted from the object space of measurement R passes the fluorescence selection filter 213 of the fluorescence mirror unit 210 and enters the condenser lens 204. Then, the light that enters the condenser lens 204 is focused or converged by the condenser lens 204. The photodetector 205 is arranged at the focal point or the converging point. Therefore, fluorescence is detected by the photodetector 205. The photodetector 205 may be selected typically from a photodiode, a photomultiplier and a cooled CCD.

As pointed out above, the microchip 100 is mounted on a stage (not shown). Additionally, the first mirror 221 and the second mirror 222 are arranged with the microchip 100 interposed between them. Thus, the two mirrors 221 and 222 are arranged near the object space of measurement R of the microchip 100 and the object space of measurement R is interposed between them. As shown in FIG. 2, the mirror located at the opposite side of the object space of measurement R relative to the fluorescence mirror unit 210 is the first mirror 221, whereas the mirror located at the same side of the object space of measurement R relative to the fluorescence mirror unit 210 is the second mirror 222. The first mirror 221 is a concave mirror as shown in FIG. 2 and the focal length of the concave mirror is f1. The second mirror 222 is also a concave mirror as shown in FIG. 2 and the focal length of the concave mirror is f2.

The diameter of the second mirror 222 is smaller than the diameter of the flux of collimated light that gets to the second mirror 222. Of the flux of collimated light getting to the second mirror 222, rays of light located in a central area are blocked by the second mirror 222. On the other hand, rays of light located in a peripheral area pass an outer peripheral part of the second mirror 222 and enter the microchip 100. Thus, as a result, a tubular flux of collimated light enters the microchip 100. The object space of measurement R is located at a position facing the second mirror 222. Therefore, the tubular flux of collimated light does not get to the object space of measurement R.

The tubular flux of light that enters the microchip 100 then passes through the microchip 100. The diameter of the first mirror 221 is greater than that of the second mirror 222. The expression of "the diameter of the first mirror 221" refers to the length that is twice of the distance between the outermost position of the reflection surface of the first mirror 221 and the optical axis of the first mirror 221. The tubular flux of collimated light that strikes the first mirror 221 is reflected by the first mirror 221 toward the microchip 100. Since light is reflected by a concave surface, the reflected tubular flux of light is converged to the object space of measurement R. As a result, the object space of measurement R is irradiated with light.

Preferably, the diameter of the first mirror 221 is same as or great than that of the flux of collimated light. While the diameter of the first mirror 221 may be smaller than the diameter of the flux of collimated light, the efficiency of utilization of light is reduced with such an arrangement because the tubular flux of collimated light is reflected only partly.

In this embodiment, light from the light source 201 strikes the excitation light selection filter 211 of the fluorescence mirror unit 210. Then, as a result, only excitation light that is necessary is allowed to enter the microchip 100. Subsequently, excitation light passes through the microchip 100 and gets to the first mirror 221. Light that gets to the first mirror 221 is reflected by the first mirror 221 and converged to the inside of the flow channel in the object space of measurement R as shown in FIG. 2. Then, excitation light is partly absorbed by the sample existing in the flow channel in the object space of measurement R. Thus, as a result, fluorescence is generated from the sample.

On the other hand, excitation light that is not absorbed by the sample then passes through the microchip 100 and gets to the second mirror 222. Excitation light that gets to the second mirror 222 is reflected by the second mirror 222. At this time, since scattered light is reflected by the concave surface of the second mirror 222, reflected excitation light is collimated before it gets to the first mirror 221. In this way, excitation light is repeatedly reflected by the first mirror 221 and the second mirror 222.

Fluorescence generated in the flow channel is reflected and collimated by the first mirror 221. However, of the flux of collimated fluorescence, the part that strikes the second mirror 222 is blocked by the second mirror 222. Thus, fluorescence that enters the fluorescence mirror unit 210 becomes a tubular flux of collimated fluorescence just like excitation light. After passing through the fluorescence mirror unit 210, the tubular flux of collimated fluorescence enters the photodetector 205.

In this way, fluorescence is generated from the fluorescent substance in the sample (object of examination) existing in the object space of measurement R as the sample is irradiated by excitation light and then passes through the fluorescence mirror unit 210 before it is detected by the photodetector 205. Note that excitation light coming out from the microchip 100 and directed toward the photodetector 205 does not get to the photodetector 205 because it is blocked by the fluorescence selection filter 213 of the fluorescence mirror unit 210.

With the above-described arrangement, excitation light is repeatedly converged onto the sample (object of examination) existing in the object space of measurement R so that the intensity of fluorescence can be boosted to make it possible to measure the intensity of fluorescence with a high S/N ratio if the concentration of the fluorescence substance contained in the sample (object of examination) is low. Then, as a result, the time required for the measurement can be reduced. Now, desired measurement conditions for the first mirror 221, the second mirror 222 and the microchip 100 will be discussed below.

Figure 3:
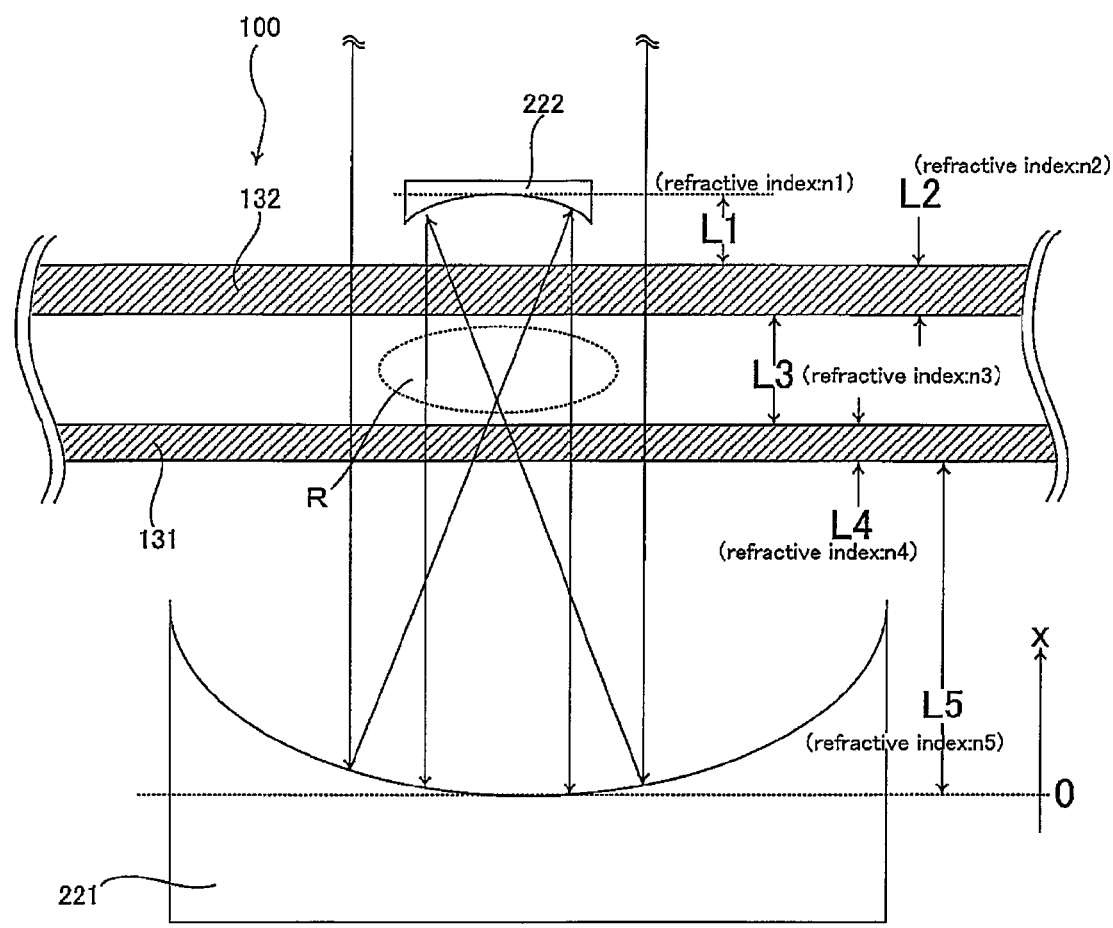
FIG. 3 is a schematic illustration of the detecting section of the measuring device according to the embodiment of FIG. 1.

FIG. 3 is a schematic illustration of the detecting section of the measuring device of this embodiment. As shown in FIG. 3, the distance between the second mirror 222 and the second substrate 132 (the distance between the position of reflection of the second mirror 222 on the optical axis thereof and the surface of the second substrate 132 at the side of the second mirror 222) is L1 and the space between them is filled with a first medium showing a refractive index n1. The second substrate 132 has a thickness of L2 and is filled with a substance showing a refractive index n2. The distance between the second substrate 132 and the first substrate 131 (the distance between the surface of the second substrate 132 at the side of the first mirror 221 and the surface of the first substrate 131 at the side of the second mirror 222) is L3 and the space between them is filled with a sample solution showing a refractive index n3 when the fluorescence of the sample is measured. The first substrate 131 has a thickness of L4 and is formed by a substance showing a refractive index n4. The distance between the first substrate 131 and the first mirror 221 (the distance between the surface of the first substrate 131 at the side of the first mirror 221 and the position of reflection of the first mirror 221 on the optical axis thereof) is L5 and the space between them is filled with a medium showing a refractive index n5. Normally, both the medium between the second mirror 222 and the second substrate 132 and the medium between the first substrate 131 and the first mirror 221 are air, n1=n5=1. Also as shown in FIG. 3, the distances L1 through L5 are expressed by means of an x-axis coordinate where the bottom position of the concaved surface of the first mirror 221, which is a concave mirror, (the position of reflection of the first mirror 221 on the optical axis thereof) is defined as 0 position (origin) and the x-axis coordinate takes positive values at positions above the 0 position.

With the above definitions, the distance L between the second mirror 222 and the first mirror 221 in terms of distance in air is expressed by the formula (1) shown below.

$$L = L1/n1 + L2/n2 + L3/n3 + L4/n4 + L5/n5 \quad (1)$$

For light reflected by the first mirror 221 and the second mirror 222 to be converged between the first substrate 131 and the second substrate 132, the focal length f1 of the first mirror 221, the focal length f2 of the second mirror 222 and the distance L in terms of distance in air are required to satisfy the requirement of the formula (2) shown below.

$$f1 + f2 = L \quad (2)$$

Furthermore, the requirements of the formulas (3) and (4) shown below need to be satisfied for the focused position of reflected light to be located in the inside of the object space of measurement R.

$$L4/n4 + L5/n5 < f1 < L3/n3 + L4/n4 + L5/n5 \quad (3)$$

$$L1/n1 + L2/n2 < f2 < L1/n1 + L2/n2 + L3/n3 \quad (4)$$

When the requirements of the formula (3) are satisfied, the focused position of light reflected by the first mirror 221 can be located in the inside of the object space of measurement R when collimated light gets to the first mirror 221. Additionally, when the requirements of the formula (4) are satisfied, the focused position of light reflected by the first mirror 221 can be located in the inside of the object space of measurement R. Therefore, excitation light can be converged repeatedly onto the sample (object of examination) existing in the object space of measurement R by satisfying the requirements of the formulas (1) through (4). Thus, the intensity of fluorescence can be boosted to make it possible to measure the intensity of fluorescence with a high S/N ratio if the concentration of the fluorescence substance contained in the sample (object of examination) is low.

Now, another embodiment of the present invention will be described below. The first mirror 221 and the second mirror 222 of this embodiment are cylindrical mirrors. The two cylindrical mirrors are arranged such that their curvatures (generatrices) are aimed at the same direction. Thus, excitation light is converged to form a line in the sample in the flow channel in the object space of measurement R of this embodiment. In other words, this embodiment provides an effect similar to an arrangement for measuring the fluorescence of sample (object of examination) in the flow channel at a number of points that are arranged on a line to make it possible to reduce the influence of the concentration unevenness or the concentration gradient, if any, of the sample. Note that a cylindrical mirror has a reflection surface formed by a part of the lateral surface of a circular cylinder. The circular cylinder has a central axis. The first mirror 221 and the second mirror 222 need to be arranged with their central axes running in parallel with each other. The optical axis of the first mirror 221 and that of and second mirror 222 have to be contained in a plane that contains the two central axes.

Now, still another embodiment of the present invention will be described below. The first mirror 221 and the second mirror 222 of this embodiment are paraboloidal mirrors. Light strikes a paraboloidal mirror in parallel with the axis of the paraboloidal surface of the paraboloidal mirror and rays of light reflected by the paraboloidal surface are converged to the focus of the paraboloidal surface without aberration. Conversely, rays of light radiated from the focus of a paraboloidal surface are reflected by the paraboloidal surface to become parallel rays of light that are parallel relative to the axis of the paraboloidal surface. Therefore, in this embodiment, excitation light reflected by the first mirror 221 and converged to the focus of the first mirror 221 strikes the second mirror 222 and is reflected to become collimated light once again. Then, as a result, excitation light is transmitted through a same position of the sample (object of examination) in the object space of measurement R repeatedly to consequently raise the efficiency of utilization of excitation light. Then, weak fluorescence can be boosted and detected efficiently.

Figure 4:
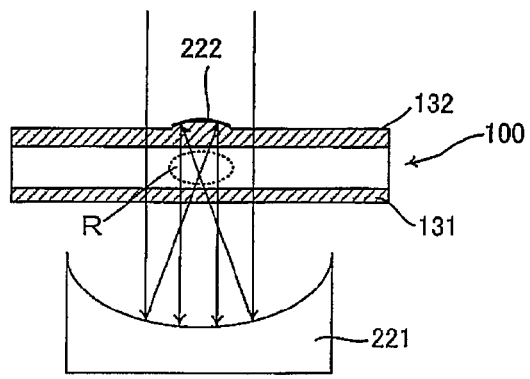
FIG. 4 is a schematic illustration of measuring device according to another embodiment of the present invention, including a cross-sectional view of the detecting section of the measuring device.

Now, still another embodiment of the present invention will be described below. FIG. 4 is a schematic illustration of the measuring device of this embodiment, including a cross-sectional view of the detecting section of the measuring device. As shown in FIG. 4, the second mirror 222 of this embodiment is integrally molded with the microchip 100. Therefore, the distance from the focused point of excitation light to the second mirror 222 of this embodiment is reduced to make it possible to downsize the second mirror 222. Then, the loss of the quantity of light that is produced as the second mirror 222 partly blocks light striking the first mirror 221 can be reduced. Additionally, the loss of the quantity of fluorescence reflected by the first mirror 221 that is produced as it the second mirror 222 partly blocks fluorescence emitted from the first mirror 221 can also be reduced. Thus, this embodiment of which the second mirror 222 is integrally molded with the microchip 100 can boost weak fluorescence and detect fluorescence further efficiently.

Now, still another embodiment of the present invention will be described below. In this embodiment, the second mirror 222 has such the wavelength characteristic that it reflects excitation light and transmits fluorescence. More specifically, a dichroic mirror is employed for the second mirror 222. Then, fluorescence generated from the sample (object of examination) in the object space of measurement R in this embodiment can be transmitted through the second mirror 222 to make it possible to detect fluorescence further efficiently.

Figure 5:
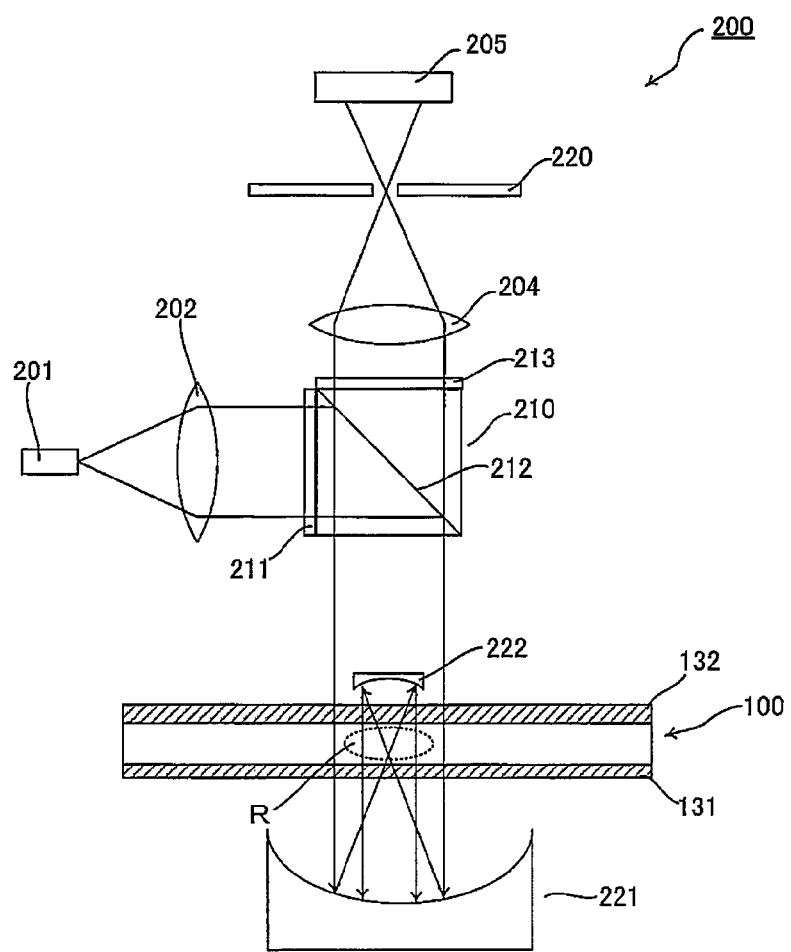
FIG. 5 is a schematic illustration of measuring device according to still another embodiment of the present invention, including a cross-sectional view of the detecting section of the measuring device.

Now, still another embodiment of the present invention will be described below. FIG. 5 is a schematic illustration of measuring device according to still another embodiment of the present invention, including a cross-sectional view of the detecting section of the measuring device. This embodiment differs from the embodiment illustrated in FIG. 2 in that a pinhole 220 is arranged in front of the photodetector 205 for receiving fluorescence to form a confocal optical system. In other words, the pinhole 220 is arranged between the condenser lens 204 and the photodetector 205. More specifically, the pinhole 220 is arranged at the conjugate position of the focused point of excitation light. A laser may be employed as light source.

As excitation light enters the microchip 100, the microchip 100 itself can radiate fluorescence, which is referred to as auto-fluorescence, to produce background noise. However, auto-fluorescence that the microchip 100 produces can be prevented from entering the photodetector 205 as noise by arranging such a confocal optical system. Thus, the present embodiment can further raise the S/N ratio of fluorescence.

Figure 6:
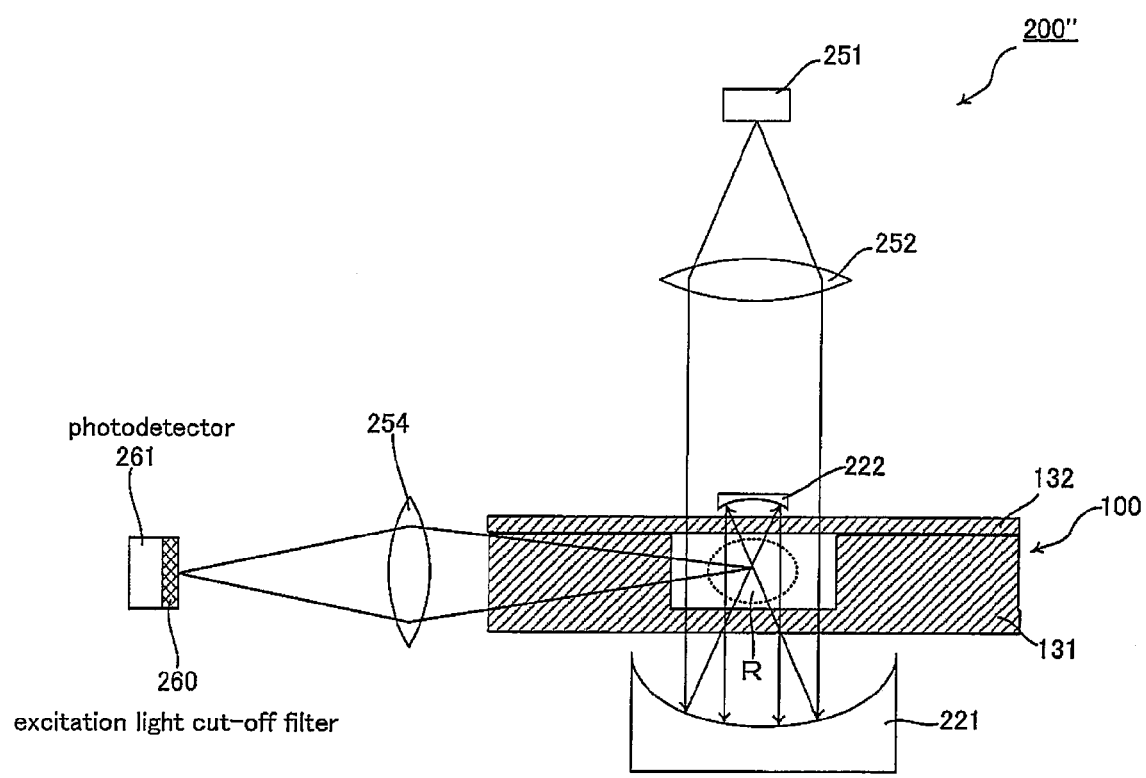
FIG. 6 is a schematic illustration of measuring device according to still another embodiment of the present invention, including a cross-sectional view of the detecting section of the measuring device.

Now, still another embodiment of the present invention will be described below. FIG. 6 is a schematic illustration of this embodiment of measuring device, including a cross-sectional view of the detecting section of the measuring device. The embodiment of FIG. 6 is adapted to measure fluorescence in a direction perpendicular to the optical axis of excitation light.

In FIG. 6, 251 denotes a light source and 252 and 254 respectively denote a collimator lens and a condenser lens, while 260 denotes an excitation light cut-off filter and 261 denotes a photodetector. Since the components denoted by the reference symbols same as those in FIG. 2 respectively have the same configurations, they will not be described here any further.

In this embodiment, excitation light emitted from the light source 251 is collimated by the collimator lens 252 and enters the object space of measurement R of the microchip 100 that is placed between the first mirror 221 and the second mirror 222. The focusing effect of the first mirror 221 and that of the second mirror 222 are same as those described above.

In this embodiment, fluorescence radiated from the sample (object of examination) in the object space of measurement R is observed from a direction perpendicular to the optical axis of incident light. More specifically, the excitation light cut-off filter 260 is arranged in front of the photodetector 261. The condenser lens 254 is arranged at a position that establishes a conjugate relationship with the focused point of excitation light and the photodetector 261.

This embodiment having the above-described configuration can prevent any loss of light by the second mirror 222 and efficiently detect fluorescence by means of the photodetector 261 in addition to the advantages described above for the preceding embodiments.

Figure 7:
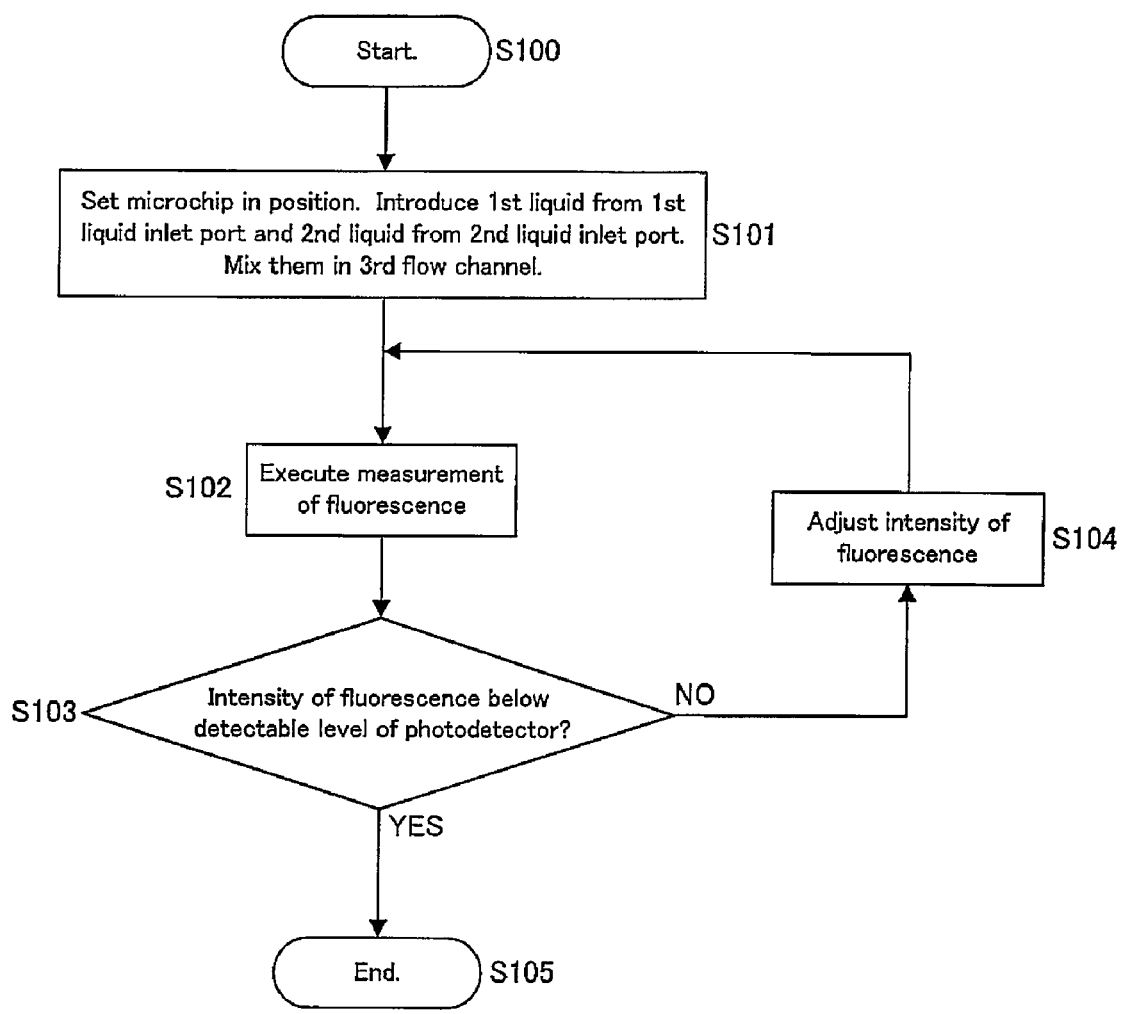
FIG. 7 is a flowchart of the measuring operation of measuring method according to the embodiment of the present invention.

Now, a measuring method according to the present invention will be described below that is adapted to use a measuring device having any of the above-described configurations will be described below. FIG. 7 is a flowchart of the measuring operation of an embodiment of measuring method according to the present invention.

Referring to FIG. 7, the measuring operation starts in Step S100. Subsequently, in Step S101, a microchip 100 is set in position in the measuring device 200. A first liquid and a second liquid are introduced respectively from the first liquid inlet port 111 and from the second liquid inlet port 112 and then mixed together in the third flow channel 123, while a sample (object of examination) is introduced into the object space of measurement R. In Step S102, fluorescence radiated from the sample (object of examination) is measured.

In Step S103, it is determined if the intensity of fluorescence is below the detectable limit level of the photodetector (205, 261) or not. If the answer to the question in Step S103 is YES, the operation proceeds to Step S105 to end the measuring process.

If, on the other hand, the answer to the question in Step S103 is NO, the operation proceeds to Step S104, where the intensity of fluorescence is adjusted in the measuring system. Then, fluorescence is measured again in Step S102.

Thus, according to the present embodiments, fluorescence can be detected with a high S/N ratio as the measuring operation is conducted while the intensity of fluorescence is adjusted.

Techniques for adjusting the intensity of fluorescence for the purpose of the present invention include arranging an ND filter on the optical path of the measuring system, lowering the output level of the light source if the output level of the light source is variable, lowering the gain of the photodetector, reducing the exposure time of the photodetector and using combinations of any of the above listed techniques.

Thus, with a measuring device and a measuring method according to the present embodiments, excitation light can be converged repeatedly onto the sample (object of examination) existing in the object space of measurement R. Then, as a result, the intensity of fluorescence can be boosted and observed with a high S/N ratio if the concentration of the fluorescent substance is low in the sample (object of examination). Therefore, the measuring time can be reduced.

While the present invention is described by way of different embodiments, any combinations of the above-described embodiments are also within the spirit and scope of the present invention.

What is claimed is:

1. A measuring device comprising:
a light source;
a holding member for holding a sample;
a first concave mirror; and
a second concave mirror; wherein
the second concave minor being arranged on the light path from the light source to the holding member;
the first concave minor being arranged vis-a-vis the second concave minor with the holding member interposed between them;
the first concave minor and the second concave minor being arranged with their concave surfaces facing each other;
the first concave mirror being larger than the second concave minor in terms of their outer dimensions.

2. The device according to claim 1, wherein
the first concave minor and the second concave minor are arranged in such a way that their focal positions agree with each other.

3. The device according to claim 2, further comprising an optical system arranged between the light source and the first concave mirror to collimate light emitted from the light source, the diameter of the flux of collimated light being greater than the diameter of the second concave minor.

4. The device according to claim 3, wherein
the first concave mirror and the second concave mirror are cylindrical mirrors and the curvatures of the two cylindrical mirrors are aimed at the same direction.

5. The device according to claim 3, wherein
the first concave mirror and the second concave mirror are paraboloidal mirrors.

6. The device according to claim 2, wherein the first concave minor and the second concave mirror are cylindrical mirrors and the curvatures of the two cylindrical mirrors are aimed at the same direction.

7. The device according to claim 2, wherein the first concave mirror and the second concave mirror are paraboloidal mirrors.

8. The device according to claim 1, wherein
the first concave minor and the second concave mirror are cylindrical mirrors and the curvatures of the two cylindrical mirrors are aimed at the same direction.

9. The device according to claim 1, wherein
the first concave mirror and the second concave mirror are paraboloidal mirrors.

10. A measuring method comprising:
a first irradiation step of making a tubular flux of collimated light strike a sample from one of the opposite sides thereof;
a second irradiation step of reflecting the flux of collimated light toward the sample after passing through the sample and focusing it in the sample;
a third irradiation step of reflecting light emitted from the sample, while being scattered, collimating it and making it strike the sample from the other side;
the second irradiation step and the third irradiation step being repeated before detecting light from the sample.

* * * * *